(12) United States Patent
Paul et al.

(10) Patent No.: US 7,662,180 B2
(45) Date of Patent: Feb. 16, 2010

(54) ACCOMMODATING INTRAOCULAR LENS AND METHOD OF MANUFACTURE THEREOF

(75) Inventors: Marlene L. Paul, Laguna Niguel, CA (US); Michael D. Lowery, Vista, CA (US); Daniel Brady, San Juan Capistrano, CA (US); Arlene Gwon, Newport Beach, CA (US)

(73) Assignee: Abbott Medical Optics Inc., Santa Ana, CA (US)

( * ) Notice: Subject to any disclaimer, the term of this patent is extended or adjusted under 35 U.S.C. 154(b) by 1183 days.

(21) Appl. No.: 10/314,069

(22) Filed: Dec. 5, 2002

(65) Prior Publication Data

US 2004/0111151 A1 Jun. 10, 2004

(51) Int. Cl.
*A61F 2/16* (2006.01)

(52) U.S. Cl. .................................. 623/6.56; 623/6.38

(58) Field of Classification Search ....... 623/6.11–6.56; 264/1.7
See application file for complete search history.

(56) References Cited

U.S. PATENT DOCUMENTS

| RE25,286 | E |   | 11/1962 | De Carle |             |
|----------|---|---|---------|----------|-------------|
| 3,415,597 | A |   | 12/1968 | Harman |             |
| 4,102,567 | A | * | 7/1978 | Cuffe et al. | 351/160 R |
| 4,576,607 | A | * | 3/1986 | Kelman | 623/6.5 |
| 4,624,669 | A |   | 11/1986 | Grendahl |             |
| 4,646,720 | A |   | 3/1987 | Peyman et al. |             |
| 4,666,444 | A | * | 5/1987 | Pannu | 623/6.45 |
| 4,828,558 | A | * | 5/1989 | Kelman | 623/6.13 |
| 4,890,912 | A |   | 1/1990 | Visser |             |
| 5,044,742 | A |   | 9/1991 | Cohen |             |
| 5,054,905 | A |   | 10/1991 | Cohen |             |
| 5,056,908 | A |   | 10/1991 | Cohen |             |
| 5,123,921 | A |   | 6/1992 | Werblin et al. |             |
| 5,133,749 | A | * | 7/1992 | Nordan | 623/6.49 |
| 5,180,390 | A | * | 1/1993 | Drews | 623/6.4 |
| 5,196,026 | A |   | 3/1993 | Barrett et al. |             |
| 5,217,491 | A | * | 6/1993 | Vanderbilt | 623/6.46 |
| 5,258,025 | A |   | 11/1993 | Fedorov et al. |             |
| 5,336,261 | A |   | 8/1994 | Barrett et al. |             |
| 5,376,694 | A | * | 12/1994 | Christ et al. | 523/113 |
| 5,489,301 | A |   | 2/1996 | Barber |             |
| 5,608,471 | A |   | 3/1997 | Miller |             |
| 5,650,837 | A |   | 7/1997 | Roffman et al. |             |
| 5,695,509 | A |   | 12/1997 | El Hage |             |
| RE36,150 | E | * | 3/1999 | Gupta | 623/6.56 |
| 5,876,441 | A | * | 3/1999 | Shibuya | 623/6.56 |

(Continued)

OTHER PUBLICATIONS

Lane et al., "Polysulfone Intracorneal Lenses", *Int Ophthalmol Clin.*, 1991 31: pp. 37-46.

(Continued)

*Primary Examiner*—Corrine McDermott
*Assistant Examiner*—Cheryl Miller

(57) ABSTRACT

An accommodating IOL comprises an optic adapted to focus light toward a retina of an eye, and a movement assembly coupled to the eye to provide effective accommodating movement, preferably axial movement, of the optic. At least a portion of the movement assembly is made from a material that is less stiff and/or more resilient than the material used to make the optic. Optionally, an outer ring or support portion made at least partially from either a relatively stiff material such as the material used in the optic or a relatively resilient material such as the material used in the movement assembly is also provided.

27 Claims, 2 Drawing Sheets

U.S. PATENT DOCUMENTS

| | | | |
|---|---|---|---|
| 6,015,435 | A | 1/2000 | Valunin et al. |
| 6,090,141 | A | 7/2000 | Lindstrom |
| 6,102,946 | A | 8/2000 | Nigam |
| 6,106,553 | A | 8/2000 | Feingold |
| 6,197,059 | B1* | 3/2001 | Cumming .................. 623/6.39 |
| 6,231,603 | B1* | 5/2001 | Lang et al. ................. 623/6.37 |
| 6,425,917 | B1* | 7/2002 | Blake ........................ 623/6.42 |
| 6,488,708 | B2* | 12/2002 | Sarfarazi ................... 623/6.34 |
| 6,645,246 | B1* | 11/2003 | Weinschenk et al. ....... 623/6.37 |
| 6,695,881 | B2* | 2/2004 | Peng et al. ................. 623/6.34 |
| 2002/0103536 | A1* | 8/2002 | Landreville et al. ........ 623/6.37 |
| 2003/0187505 | A1* | 10/2003 | Liao .......................... 623/6.37 |
| 2004/0002757 | A1* | 1/2004 | Lai et al. ................... 623/6.16 |
| 2004/0249456 | A1* | 12/2004 | Cumming .................. 623/6.37 |

OTHER PUBLICATIONS

McCarey et al., "Modeling Glucose Distribution in the Cornea", Article from Dept. of Ophthalmology and Anatomy, Emory University School of Medicine vol. 9 No. 11 p. 1025-1039, 1990.

\* cited by examiner

ACCOMMODATING INTRAOCULAR LENS AND METHOD OF MANUFACTURE THEREOF

This invention relates to intraocular lenses (IOLs). More particularly, the invention relates to intraocular lenses which provide accommodating movement in the eye.

The human eye is susceptible to numerous disorders and diseases, a number of which attack the crystalline lens. For example, cataracts mar vision through cloudy or opaque discoloration of the lens of the eye, and can result in partial or complete blindness. When this happens, the crystalline lens can be removed and replaced with an intraocular lens, or IOL. A typical IOL comprises an optic body, or lens, adapted to focus light toward the retina of the eye, and one or more fixation members, or haptics, adapted to secure the IOL in a relatively fixed position in a suitable location such as the anterior chamber, iris, or capsular bag of the eye.

The optic and haptics may be formed as an integral unit from a single material, but in recent years the trend has been toward composite IOLs which use different materials for the various components, so that the properties of these components can be separately optimized. Examples of such composite IOLs are shown in Barrett U.S. Pat. No. 4,997,442 and Vanderbilt U.S. Pat. No. 5,217,491, both of which employ relatively flexible materials in the optic portion and more rigid materials in the haptics. The disclosure of each of these patents is incorporated in its entirety herein by reference.

One drawback of conventional IOLs has been that, while they provide suitable correction for normal distance vision, they do not provide effective accommodation, i.e. the ability to refocus the eyes as needed for viewing both near and distant objects. Until fairly recently, the only solution was to wear eyeglasses, but other options are now available. For instance, multifocal IOLs have been designed for providing near, far, and intermediate vision. In addition, IOLs have been provided with movement assemblies which cooperate with the ciliary muscles and/or other structures of the eye to move the optic axially between near and far vision positions. Examples of this latter class of IOLs, referred to broadly as accommodating IOLs, can be found in Levy U.S. Pat. No. 4,409,691, Cumming U.S. Pat. Nos. 5,674,282; 5,496,366; 6,197,059 and 6,387,126, Gwon et al. U.S. Pat. No. 6,176,878, Lang et al. U.S. Pat. No. 6,231,603, and Laguette et al. U.S. Pat. No. 6,406,494. The disclosure of each of these patents is incorporated in its entirety herein by reference.

The aforementioned references are concerned primarily with the geometry and mechanical configuration of various accommodating IOLs, but deal only cursorily, if at all, with material selection and manufacturing issues. Certain general properties of the IOL components such as, for instance, flexibility of the movement assembly, are described as being preferred or desirable, but are not delineated in absolute or relative terms.

Among the objects of this invention, are certain aspects of the novel enhanced design of an accommodating IOL from an appropriate combination of materials which provides at the same time optimum optical qualities, increased accommodation ability, and, sufficient flexibility to allow the IOL to be inserted through a small incision in an eye, without a concomitant loss in accommodative functionality.

A further object of the invention is to provide novel enhanced methods for manufacturing the IOLs, which methods overcome the deficits in the prior art, and address the longstanding needs that shall become visible to artisans upon reading of the claims which are appended hereto, in light of the teachings of the present invention set forth herein.

SUMMARY OF THE INVENTION

The present invention provides new and enhanced accommodating intraocular lenses (IOLs). Methods of manufacturing these enhanced IOLs are also disclosed, which are leveraged off of the novel enhanced design strategies embodied in the teachings of the present invention.

In accordance with one aspect of the invention, an accommodating IOL comprises an optic portion, e.g. lens body, adapted to focus light toward a retina of an eye, and a movement assembly coupled to the optic portion or optic and effective, in cooperation with the eye, to provide effective accommodating movement, preferably axial movement, of the optic. At least a portion of the movement assembly is made from a material that is less stiff than the material used to make the optic. Preferably, both materials are polymeric materials.

The term "stiffness", as used herein, shall be understood to relate to the amount of elastic deformation a material undergoes when subjected to a given amount of force. Generally speaking, the less elastic deformation a material undergoes per unit force, the stiffer the material. If two elastic materials are subjected to the same amount of force over the same period of time, the stiffer material is the one which deforms the least. The stiffness of an elastic material, typically expressed in terms of its Young's Modulus, is the opposite of its flexibility; a material which is stiffer than another material is less flexible than that material, and vice versa.

Without wishing to be limited to any particular theory of operation, it is believed that the use of a comparatively flexible material in the movement assembly allows the relatively small forces exerted on the IOL by the zonules, ciliary muscles, and capsular bag of the eye to be translated into increased axial movement of the optic body relative to a substantially identical IOL having a movement assembly made of a comparatively stiff material. In order to provide effective accommodation for a typical presbyopic patient, this axial movement is preferably at least 0.5 mm, and more preferably, in the range of about 1.0 to about 2.5 mm.

The movement assembly may have any suitable configuration effective to cooperate with the eye to provide for effective accommodating movement of the optic, as desired. For example, the movement assembly may comprise a plurality of plate-type members, a single disk-type member, a combination of plate-type members and an outer ring, and related combinations or subcombinations. The movement assembly may include a hinge assembly. Either the hinge assembly alone or the entire movement assembly may be formed of the less stiff material, which functions to vault the optic in an accommodating way, based upon the combined modulus of the system which is created.

In one example according to the first aspect, the first and second materials both belong to the same class of polymeric materials and are derived from monomers which are mutually compatible, allowing the materials to be co-cured and/or bonded, for example chemically bonded, to one another. For instance, both materials may be acrylic polymeric materials. More specifically, the first material may be an acrylic material that, preferably, is flexible enough to be folded but stiff enough to maintain acceptable image quality. Even more specifically, the first material may be a cross-linked acrylic material, such as a material formed of copolymers of methacrylate and acrylate esters cross-linked with one or more functional acrylate/methacrylate cross-linking components. The second material may be a relatively high water content acrylic polymer in the form of a hydrogel such as, for instance, a hydroxyethyl methacrylate (HEMA) polymer or a methyl methacrylate/N-vinyl pyrrolidone (MMA/NVP) copolymer or the like.

In another example according to the first aspect, both materials may be silicon-containing polymeric materials. Preferably, the first material is a silicon-containing polymeric material including a reinforcing component, such as a silica-reinforcing agent, and the second, less stiff, material is a silicon-containing polymeric material having no reinforcing component, or a reduced amount of reinforcing component than the first material. Except for the amount of the reinforcing component, the second material may have the same formulation as the first material.

In still another example of the first aspect, the first material may be an acrylic polymeric material and the second material may be a silicon-containing polymeric material. More specifically, the first material may be a cross-linked acrylic material, such as a material formed of copolymers of methacrylate and acrylate esters cross-linked with one or more functional acrylate/methacrylate cross-linking components. The second, less stiff, material may be a silicon-containing polymeric material including a reinforcing component, such as a silica-reinforcing agent.

In accordance with a second aspect of the invention, an accommodating IOL comprises an optic portion, e.g. lens body, adapted to focus light toward a retina of an eye, and a movement assembly coupled to the optic portion or optic and effective, in cooperation with the eye, to provide effective accommodating movement, preferably axial movement, of the optic. At least a portion of the movement assembly is made from a material that is more resilient, or responsive, than the material used to make the optic. Preferably, both materials are polymeric materials.

For the purposes of this invention, the terms "resilient" and "responsive" are generally synonymous, and shall be understood to relate to the amount of time an elastic material takes to return to its original state after deformation. A material that returns relatively quickly to its original state is referred to here as a "resilient" or "responsive" material, and a material that takes longer to return to its original state is referred to as "less resilient", "less responsive", "relatively non-resilient", or "relatively non-responsive". Many of the materials referred to herein as "resilient" are also flexible; however, some resilient materials, such as polymethyl methacrylate (PMMA) are relatively stiff.

Without wishing to be limited to any particular theory of operation, it is believed that the use of a comparatively resilient material in the movement assembly allows more rapid accommodation or movement, specifically axial movement, relative to a substantially identical IOL having a movement assembly made entirely of a less resilient material. The increased speed of accommodation means that a patient provided with an enhanced accommodating IOL, according to the present invention, will be able to refocus relatively quickly when shifting from far to near vision and back again.

The movement assembly may have any suitable configuration effective to cooperate with the eye to provide for effective accommodating movement of the optic, as desired. For example, the movement assembly may comprise a plurality of plate-type members, a single disk-type member, a combination of plate-type members and an outer ring, and the like. The movement assembly may include a hinge assembly. Either the hinge assembly alone or the entire movement assembly may be formed of the more resilient material.

In one example according to the second aspect, the optic may be made of a first acrylic material having no water content or a relatively low water content, and at least a portion of the movement assembly may made of a second acrylic material having a higher water content. The higher water content of the second acrylic material makes it more resilient, or responsive, than the second acrylic material. Specifically, the first acrylic material may be a cross-linked acrylic material, such as a material formed of copolymers of methacrylate and acrylate esters cross-linked with one or more functional polyacrylate/methacrylate cross-linking components. The second material may be a relatively high water content acrylic polymer in the form of a hydrogel such as, for instance, a hydroxyethyl methacrylate (HEMA) polymer or a methyl methacrylate/N-vinyl pyrrolidone (MMA/NVP) polymer and the like.

In another example according to the second aspect, the first material may be an acrylic polymeric material and the second material may be a silicon-containing polymeric material. More specifically, the first material may be a cross-linked acrylic material, such as a material formed of copolymers of methacrylate and acrylate esters cross-linked with one or more functional acrylate/methacrylate cross-linking components. The second material may be a silicon-containing polymeric material including a reinforcing component, such as a silica-reinforcing agent.

The movement assemblies of the IOLs in any of the above examples, according to both aspects of the invention, may optionally include a distal end portion or support ring that is made from either a relatively stiff material, such as a material that is the same or similar to the material used in the optic, or a relatively resilient material, such as material that is the same or similar to the material used in the other portion or portions of the movement assembly. Alternatively, the distal end portion or support ring of the movement assembly may be made from a material is both stiff and resilient, such as polymethyl methacrylate (PMMA).

In one method of manufacturing according to the present invention, an accommodating IOL is produced by shaping a composite member into an optic adapted to focus light toward a retina of an eye, and a movement assembly coupled to the optic and adapted to cooperate with the eye to provide effective accommodating movement of the optic. The composite member includes a central region, which ultimately becomes at least a portion of the optic of the IOL and is made of a first material, and a peripheral region, which ultimately becomes at least a portion of the movement assembly and is made of a second material that is less stiff than the first material.

The step of shaping the composite member is often preceded by a step of producing the composite member. In an embodiment, the composite member is produced by polymerizing a first monomeric component to obtain the first material, and polymerizing a second component to obtain the second material.

In another method of manufacturing according to the present invention, an accommodating IOL is produced by shaping a composite member into an optic adapted to focus light toward a retina of an eye, and a movement assembly coupled to the optic and adapted to cooperate with the eye to provide effective accommodating movement of the optic. The composite member includes a central region, which ultimately becomes at least a portion of the optic of the IOL and is made of a first material, and a peripheral region, which ultimately becomes at least a portion of the movement assembly and is made of a second material that is more resilient than the first material.

The step of shaping the composite member is often preceded by a step of producing the composite member. In an embodiment, the composite member is produced by polymerizing a first monomeric component to obtain the first material, and polymerizing a second component to obtain the second material.

In either of these methods, if the first and second materials have compatible monomeric components, the materials can be co-cast and co-cured and/or bonded, for example, chemically bonded. If the first and second materials do not have compatible monomeric components, the second material is preferably insert molded around the first material.

The composite member may be in the form of a rod, button, or sheet which may be machined, lathed, milled, or the like to form the optic and movement assembly.

Each and every feature described herein, and each and every combination of two or more of such features, is included within the scope of the present invention provided that the features included in such a combination are not mutually inconsistent to one of normal skill in the art given the disclosures of the present invention in their entirety.

Additional aspects and advantages of the present invention are set forth in the following description and claims, particularly when considered in conjunction with the accompanying drawings in which like parts bear like reference numerals.

DETAILED DESCRIPTION OF THE DRAWINGS

Figure 1:
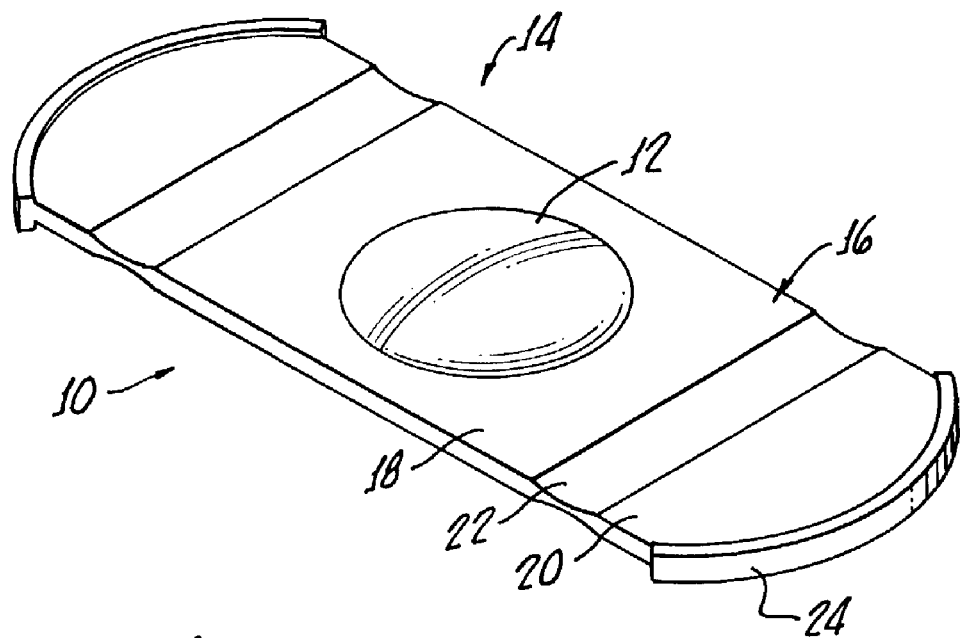
FIG. 1 is a top side view, in perspective, of an IOL in accordance with the present invention.

Referring now to FIG. 1, an accommodating IOL according to the present invention, shown generally at 10, includes a lens body or optic 12. A generally rectangular movement assembly 14 is provided for positioning the optic 12 within the capsular bag of an eye, and for cooperating with the eye to provide accommodating movement of the optic 12. The movement assembly 14 comprises a pair of plate members 16 extending from diametrically opposite edges of the optic 12. The plate members 16 are generally conventional in configuration and may be similar in structure to any of the accommodating plate haptics shown in Cumming U.S. Pat. No. 5,674,282.

The optic 12 is according to the present invention formed of a material having an appropriate balance of superior optical characteristics, flexibility, elasticity, elastic memory and tensile strength. One material meeting these requirements is that acrylic material from which the optic of an IOL marketed under the trademark SENSAR® by Advanced Medical Optics of Santa Ana, Calif. is made. Specifically, the SENSAR® brand of IOL is made of a cross-linked acrylic material formed of copolymers of methacrylate and acrylate esters, cross-linked with a diacrylate ester to produce a cross-linked acrylic copolymer. Useful cross-linked acrylic materials are disclosed in Gupta U.S. Reissue Pat. No. 36,150, the disclosure of which is expressly incorporated entirely herein by reference. Such cross-linked acrylic materials have a stiffness, expressed in terms of Young's Modulus, in the range of 1000 to 3000 PSI at body temperature.

Typically, the materials disclosed by Gupta return to their original shape (and optical resolution) within about 20 to about 180 seconds after deformation, which, for the purposes of this invention, classifies it as relatively non-responsive or non-resilient.

An alternate preferred material for the optic 12 is a silicon-containing polymeric material identified as SLM-2 and included in IOLs sold by Advanced Medical Optics of Santa Ana, Calif. Specifically, SLM-2 is a crossed-linked siloxane polymer containing 12 to 18 mol percent of aryl siloxane units, and silica reinforcer material in an amount in the range of about 15 to about 45 parts per 100 parts, by weight, of the polymer.

This material has a stiffness, as expressed by its Young's Modulus, in the range of at least about 500 to 750 psi. Further details of this material are disclosed in Christ et al. U.S. Pat. Nos. 5,236,970, 5,376,694 and 5,494,946. The disclosure of each of these is incorporated in herein by reference.

Each of the plate members 16 includes a proximal portion 18 joined to the optic 12 and a distal portion 20. Optionally, a hinge means 22 may be provided between the proximal portion 18 and the distal portion 20. Also optionally, the distal portion 20 may include a thickened distal end 24 that is contoured to accurately conform to the inner wall of the capsular bag. This thickened distal end 24 is believed to be especially effective in transmitting the forces exerted by the surrounding zonules, ciliary muscle, and capsular bag to the optic 12.

In one embodiment of the invention, each of the plate members 16 is made entirely of a material which is less stiff and/or more resilient than the material used in the optic 12. In another embodiment, the proximal and distal portions 18, 20 of the plate members 16 are made of the same material as the optic 12, while only the hinge means 22 is made of a less stiff and/or more resilient material. In yet another embodiment, the thickened distal end 24 is made of a material that is stiffer than the other portions of the plate members 16 and/or is more resilient than the material of the optic 12.

For example, in the case where at least a portion the optic 12 is made of the material used in making the SENSAR® brand of IOL, at least a portion of the plate members 16 may be formed of an acrylic material having a relatively high water content. For the purposes of this example, the water content of the acrylic material is at least about 22%, more preferably at least about 38%. Likewise, for the purposes of this example, the acrylic material is a hydrophilic hydrogel-forming material selected from the group consisting of poly hydroxyalkyl methacrylates, for example, polyhydroxyethyl methacrylate (poly HEMA) and the like, methyl methacrylate/N-vinyl pyrrolidone-containing copolymers (MMA/NVP copolymers) and mixtures thereof. For instance, either poly HEMA or MMA/NVP may be selected. The MMA/NVP copolymers may be preferred due to potentially lower levels of calcification.

The aforementioned acrylic hydrogels are known to be less stiff (i.e. more flexible) and more resilient than the cross-linked acrylic material of which the SENSAR® brand of IOLs are made. In addition, poly HEMA and MMA/NVP copolymers are derived from monomeric components that are compatible with the monomeric components from which such cross-linked acrylic materials are made.

Because of the compatibility between the monomeric components of the aforementioned acrylic hydrogels and the cross-linked acrylic material, the materials can easily be co-cured with and/or chemically bonded to each other. For instance, in one method of manufacture, the resilient portion of the IOL 10 is formed by polymerizing a precursor material, for instance a hydrogel-forming acrylic precursor material, in a mold. After polymerization, a hole is bored in the acrylic hydrogel-forming material, and a different precursor material, for instance a cross-linked acrylic precursor material, is polymerized in the hole to form a button having a relatively stiff, cross-linked acrylic core surrounded by a less stiff, or more flexible, acrylic hydrogel sheath. The sheath portion of the button is then milled to form the movement assembly 14 and the core is lathed as desired to form the optic 12 of the IOL 10.

Alternatively, the polymer forming the movement assembly is polymerized around a rod having the diameter desired of the optic. The rod is then removed and the polymer forming the optic is polymerized within the resulting space. The IOL is then lathed and milled as in the previous method. Manufacturing processes similar to this and the method outlined above are described in greater detail in Barrett U.S. Pat. No. 4,997,442 and Vanderbilt U.S. Pat. No. 5,217,491, the disclosures of both of which are incorporated by reference herein.

In still another similar method, the different polymers may be co-cast as sections of a sheet, rather than a rod or button.

In the case where the optic 12 is made from a silicon-containing polymeric material, at least a portion of the plate members 16 may be made from a less stiff silicon-containing polymeric material. For instance, if the optic 12 is made from the aforementioned SLM-2 material, at least a portion of the plate haptics 16 could be made from a material having substantially the same formulation as SLM2, but with a reduced amount of the silica-reinforcing agent. Because of the reduction of the silica-reinforcing agent, the plate members 16 are more flexible relative to the optic 12, and are thus able to effect more axial movement of the optic 12 than if the plate members 16 were made of a material having exactly the same formulation as the optic 12.

A one-piece IOL 10 having the optic 12 made from a silicon-containing polymeric material and at least a portion of the movement assembly 14 made from a less stiff silicon-containing polymeric material could be co-molded or insert molded using conventional manufacturing techniques well known in the art.

Yet another embodiment of the IOL 10 includes an optic 12 formed of a relatively stiff foldable acrylic polymeric material such as the aforementioned cross-linked acrylic polymeric material, and at least a portion of the movement assembly made of a less stiff silicon-containing material such as SLM-2. In this case, the more flexible silicon-containing polymeric material is insert molded around the stiffer acrylic polymeric material.

Figure 2:
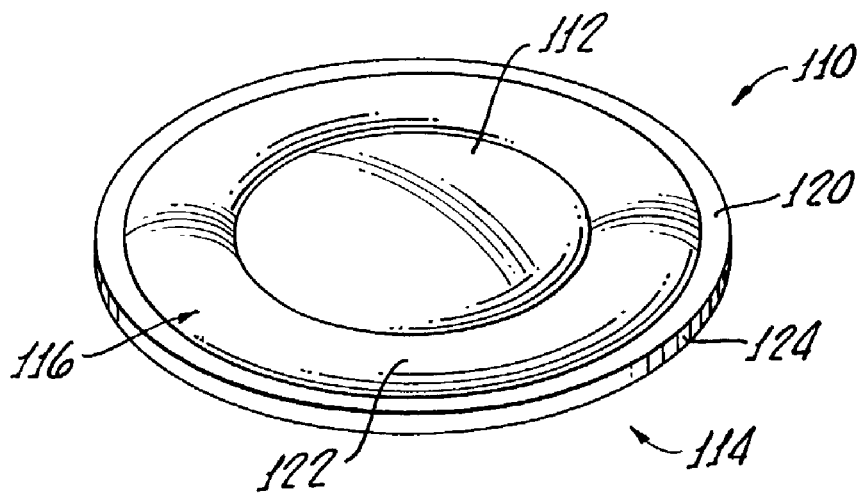
FIG. 2 is a top side view, in perspective, of an IOL in accordance with an alternate embodiment of the invention.

FIG. 2 shows an accommodating IOL 110 according to an alternate embodiment of the invention. Components of IOL 110 which correspond to components of IOL 10 are indicated by the same reference numeral increased by 100.

The IOL 110 comprises an optic 112 circumscribed by a movement assembly 114. The movement assembly 114 comprises a disc member 116 having a springy intermediate portion 122 and a distal portion 120 having a peripheral surface 124. The disc-shaped movement assembly 114 is similar in configuration to movement assemblies shown in Gwon U.S. Pat. No. 6,176,878 and Laguette et al. U.S. Pat. No. 6,406,494.

In one embodiment of the invention, the optic 112 is made from an acrylic polymeric material such as the cross-linked acrylic polymeric material described above in connection with FIG. 1. The intermediate portion 122 of the flexible member 116 is made from a less stiff and more resilient acrylic material such as one of the acrylic hydrogels mentioned above. The distal portion 120 of the flexible member 116 could be formed of the same material as the intermediate portion 122 or a stiffer material, such as the same cross-linked acrylic polymeric material used in the optic 112. Increased stiffness of the distal portion 120 may result in more effective transmission of the forces from the surrounding zonules, ciliary muscle, and capsular bag.

Alternatively, the optic 112 is made from a silicon-containing polymeric material such as the SLM-2 material described above, and at least the intermediate portion 122 of the flexible member is formed of a less stiff silicon-containing material such as one having substantially the same formulation as SLM-2 but with less silica-reinforcing agent. The distal portion 120 of the flexible member 116 could be made of either SLM-2 or the less stiff silicon-containing material.

In yet another alternative, the optic 112 could be made from a relatively stiff acrylic polymeric material such as the previously mentioned cross-linked acrylic polymeric material, and at least a portion of the flexible member 116 could be made of a less stiff silicon-containing polymeric material such as SLM-2.

Figure 3:
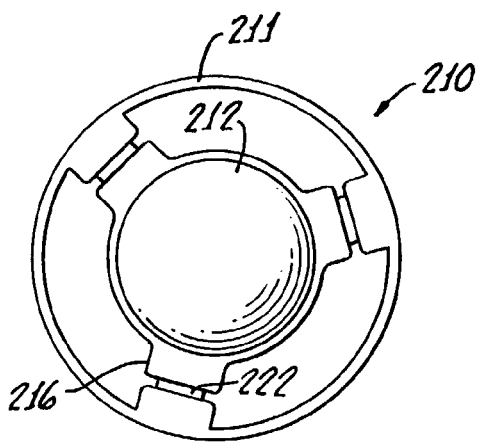
FIG. 3 is a plan view of an IOL in accordance with another alternate embodiment of the invention.

FIG. 3 shows an accommodating IOL 210 according to an especially useful embodiment of the invention. Components of IOL 210 which correspond to IOL 10 are indicated by the same reference numeral increased by 200.

The IOL 210 comprises a circular outer capsular bag support ring 211, an inner optic 212, and a plurality of radially oriented plate-like members 216 extending therebetween. Preferably, the members 216 are arranged 120° apart with substantial voids therebetween and between the optic 212 and the support ring 211. In addition, each member 216 preferably includes a reduced-thickness hinge portion 222.

While the exact configuration of the fixation members 216 is not essential to the invention, and a more solid interface rather than discrete fixation members is also acceptable, the combination of the illustrated tripod configuration, hinge portions 222 and the selection of materials as discussed herein results in particularly effective axial movement of the optic 212. Specifically, the movement assembly of IOL 210 is effective in providing an amount of axial movement in a range of about 0.5 or about 1.5 mm to about 2.0 mm or about 2.5 mm. This amount of movement is sufficient to provide in the range of about 1 to about 2.5 or about 3.5 diopters of accommodation or more, depending on various factors such as the corrective power of the optic 12. Accommodation in this range is sufficient for the majority of presbyopic patients.

As in FIGS. 1 and 2, the optic 212 of the IOL 210 may be formed of an acrylic polymeric material, such as the aforementioned cross-linked acrylic polymeric material, that is stiff enough to provide excellent optical qualities, yet flexible enough to be folded for insertion through a small incision in an eye. At least the hinge portion 222 if not the entirety of each fixation member 216 may be made of a less stiff and more resilient acrylic material, for instance an acrylic hydrogel material such as poly HEMA or MMA/NVP copolymers. The support ring 211 may be made of an acrylic polymeric material having the same or greater stiffness as the optic 212 in order to maximize transmission of forces from the zonules, ciliary muscle, and capsular bag, or it may be made of an acrylic polymeric material having the same or less stiffness than the fixation members 216 in order to maximize the amount of movement obtained from a small amount of force. The acrylic-based materials of this embodiment can easily be co-cured or bonded using manufacturing techniques similar to those discussed in connection with the acrylic-based embodiment of FIG. 1.

Alternatively, the optic 212 of the IOL 210 may be formed of a silicon-containing polymeric material such as SLM-2, and at least the hinge 222 if not the entirety of each fixation member 216 may be formed of a less stiff silicon-containing polymeric material such as one having substantially the formulation as SLM-2 but with a smaller amount of silica-reinforcing agent. The support ring 211 may be made of a silicon-containing polymeric material having the same or greater stiffness as the optic 212, or it may be made of an silicon-containing polymeric material having the same or less stiffness than the fixation members 216. A one-piece IOL 210 having all its components made from silicon-containing polymeric material as in this embodiment could be co-molded or insert molded using conventional manufacturing techniques.

In yet another alternative, the optic 212 could be made from a relatively stiff acrylic polymeric material such as the aforementioned cross-linked acrylic polymeric material, and at least a portion of each fixation member 216 could be made of a less stiff silicon-containing polymeric material such as SLM-2. Insert molding may be the most appropriate manufacturing technique for this combination of materials.

Figure 4:
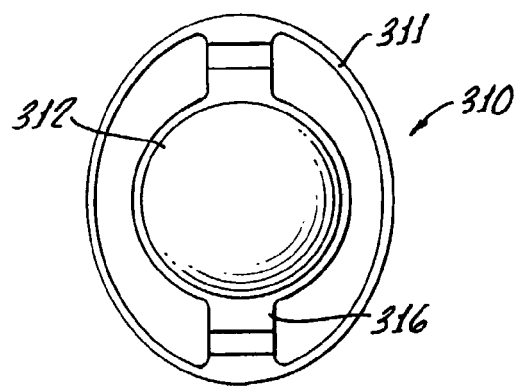
FIG. 4 is a plan view of an IOL in accordance with still another alternate embodiment of the invention.

FIG. 4 shows an IOL 310 according to yet another embodiment of the invention. Components of IOL 310 which correspond to IOL 210 are indicated by the same reference numeral increased by 100.

IOL 310 is substantially similar to IOL 210, except that only two plate-like members 316 are provided, and the support ring 311 is oval rather than circular. As in the foregoing examples, the optic 312 is made of a somewhat stiff yet preferably foldable polymeric material such as cross-linked acrylic polymeric material or SLM-2, while the members 316 are made of less stiff material such as an acrylic hydrogel material or SLM-2 in the first instance, or, in the second instance, a silica-based polymeric material containing a smaller amount of silica-reinforcing agent than SLM-2. The support ring 311 may be of a material that is the same or stiffer than the optic 312, or the same or less stiff than the fixation members 316, depending on the desired result.

Figure 5:
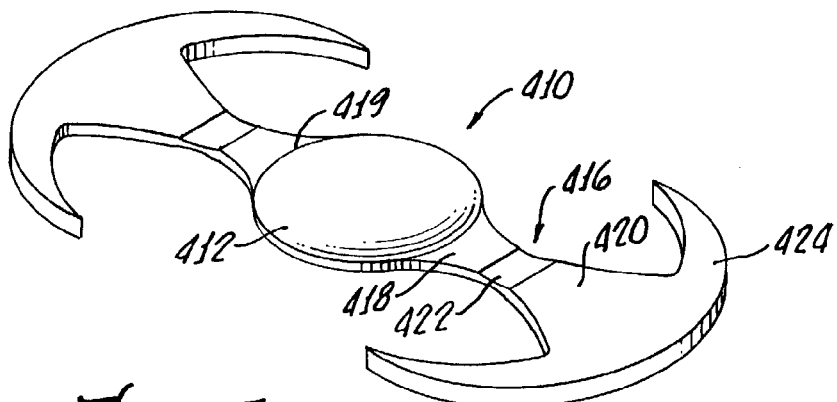
FIG. 5 is a top side view, in perspective, in accordance with yet another embodiment of the invention.

FIG. 5 shows an IOL 410 according to still another embodiment of the invention. Components of IOL 410 which correspond to IOL 10 are indicated by the same reference numeral increased by 400.

IOL 410 comprises an optic 412 and a pair of oppositely extending, generally hour-glass shaped members 416. Each member 416 includes a proximal portion 418 that gradually decreases in width from its proximal end 419 to an intermediate portion 422, and a distal portion 420 that gradually increases in width from the intermediate portion 422 to an enlarged support portion or foot 424. The intermediate portion 422 is preferably reduced in thickness and functions as a hinge. The enlarged support portion or foot 424 of each fixation member 416 is preferably curved in configuration and contoured to generally conform to the inner wall of the capsular bag.

The optic 412 is generally made of a somewhat stiff yet foldable material such as the previously mentioned cross-linked acrylic polymeric material or SLM2, but can also be made of a stiffer, non-foldable material such as PMMA. At least a portion of each fixation member 416 is made from a material that is less stiff than the optic 412. The support portion or foot 424 of each fixation member 416 is made of a material that is either stiff, resilient, or both, depending on the desired result.

For instance, in one embodiment of the invention, the optic 412 is formed from a relatively stiff acrylic polymer material such as the aforementioned cross-linked acrylic polymeric material, while at least the intermediate portion or hinge 422 of each fixation member 416 is formed from a less stiff acrylic hydrogel material such as poly HEMA or MMA/NVP copolymers. The support portion 424 may be formed at least partially from the same cross-linked acrylic polymeric material as the optic 412, or from an even stiffer but more resilient material such as milled or extruded PMMA. Alternatively, the support portion 424 may be formed of the same acrylic hydrogel material as the hinge 422 or the entirety of each fixation member 416. The components in any of these combinations of materials may be co-molded.

In another embodiment of the invention, the optic 412 is formed of SLM-2, while at least the hinge 422 of each fixation member 416 is formed of a less stiff silicon-containing material, such as a material having substantially the same formulation as SLM-2, but with a smaller amount of silica-reinforcing agent. The support portion 424 may be formed at least partially of the same SLM-2 material as the optic 412, or from a stiffer but more resilient material such as milled or extruded PMMA. Alternatively, the support portion may be formed of the same, less stiff silicon-containing material as the hinge 422 or entirety of each fixation member 416.

In still another embodiment, the optic 412 is made of an acrylic polymeric material such as the aforementioned cross-linked acrylic polymeric material, and at least a portion of each fixation member 416 is made of a less stiff, silicon-based polymeric material such as SLM-2. The support portion 424 may be formed at least partially from the same cross-linked acrylic polymeric material as the optic 412, or from an even stiffer, but more resilient material such as milled or extruded PMMA. Alternatively, the support portion 424 may be formed from the same silicon-based polymeric material as the hinge 422 or the entirety of each fixation member 416. The components in any of these combinations of materials may be insert molded.

In yet another embodiment, the optic 412 is made of PMMA, and the fixation members 416 are made of a more flexible material, for instance an acrylic hydrogel material such as polyHEMA or MMA/NVP copolymers. The support portion 424 of each fixation member 416 may be made at least partially from the same PMMA material as the optic, or the same acrylic hydrogel material as the fixation members 416. The PMMA components of an IOL 410 according to this embodiment may not be foldable for insertion through a small incision, but the loss of this characteristic may be compensated for by increased optical quality and increased resilience, leading to greater axial movement of the optic 412 and better overall accommodation.

While this invention has been described with respect to various specific examples and embodiments, it is to be understood that the invention is not limited thereto and that it can be variously practiced within the scope of the following claims.

What is claimed is:

1. An intraocular lens comprising:
an optic adapted to focus light toward a retina of an eye; and
a movement assembly coupled to the optic, at least a portion of the optic and at least a first portion of the movement assembly both being made of a first material having a first stiffness, at least a second portion of the movement assembly being made of a second material having a second stiffness, wherein the first stiffness is greater than the second stiffness;
wherein the movement assembly comprises a plurality of spaced apart plate members, each plate member including a proximal end region coupled to the optic and a distal end region extending away from the optic;
wherein the distal end regions are made at least partially of a third material which has an increased stiffness relative to the second material;

wherein the first material comprises a crosslinked acrylic polymer, and the second material comprises an acrylic hydrogel-forming polymer;
wherein the third material is a different material than the first material.

2. The intraocular lens of claim 1 which is deformable to allow passage of the intraocular lens through a small incision into an eye.

3. The intraocular lens of claim 1 which provides an increased amount of accommodating movement of the optic relative to a substantially identical intraocular lens including a movement assembly made entirely of a stiffer material than the second material.

4. The intraocular lens of claim 3, wherein the movement assembly is configured to provide axial movement.

5. The intraocular lens of claim 4, wherein the movement assembly is configured to provide at least about 0.5 mm of axial movement.

6. The intraocular lens of claim 1, wherein the first polymeric material is chemically bonded to the second polymeric material.

7. The intraocular lens of claim 1, wherein the second material has an increased water content relative to the first material.

8. The intraocular lens of claim 7, wherein the second material comprises a polymer selected from the group consisting of poly hydroxyalkyl methacrylates, methyl methacrylate/N-vinyl pyrrolidone-containing copolymers and mixtures thereof.

9. The intraocular lens of claim 1, wherein:
each plate member includes a hinge assembly positioned between the proximal end region and the distal end region; and
the hinge assembly is made of the second material.

10. The intraocular lens of claim 1, wherein the third material is stiffer than the first material.

11. The intraocular lens of claim 1, wherein the distal end region and the optic are formed partially from a same crosslinked acrylic polymeric material.

12. An intraocular lens comprising:
an optic adapted to focus light toward a retina of an eye; and
a movement assembly coupled to the optic, at least a portion of the optic and at least a first portion of the movement assembly both being made of a first material having a first stiffness, at least a second portion of the movement assembly being made of a second material having a second stiffness, wherein the first stiffness is greater than the second stiffness;
wherein the movement assembly comprises a plurality of spaced apart plate members, each plate member including a proximal end region coupled to the optic and a distal end region extending away from the optic, the movement assembly further includes an outer ring surrounding the optic and joined to the distal end regions of plate members, the outer ring being adapted to contact a capsular bag of the eye;
wherein the outer ring is made at least partially of a third material which has an increased stiffness relative to the second material.

13. The intraocular lens of claim 12 which is deformable to allow passage of the intraocular lens through a small incision into an eye.

14. The intraocular lens of claim 12 which provides an increased amount of accommodating movement of a foldable optic relative to a substantially identical intraocular lens including a movement assembly made entirely of a stiffer material than the second material.

15. The intraocular lens of claim 14, wherein the movement assembly is configured to provide axial movement.

16. The intraocular lens of claim 15, wherein the movement assembly is configured to provide at least about 0.5 mm of axial movement.

17. The intraocular lens of claim 12, wherein the first material and the second material include a first polymeric material and a second polymeric material, respectively.

18. The intraocular lens of claim 17, wherein the first and second polymeric materials are derived from monomers which are mutually compatible.

19. The intraocular lens of claim 18, wherein the first polymeric material is chemically bonded to the second polymeric material.

20. The intraocular lens of claim 17, wherein the first and second polymeric materials are both acrylic polymeric materials or both silicon-containing polymeric materials.

21. The intraocular lens of claim 20, wherein:
both the first and second materials comprise silicon-containing polymeric materials; and
the first material includes more of a reinforcing component than the second material.

22. The intraocular lens of claim 12, wherein the second material has an increased water content relative to the first material.

23. The intraocular lens of claim 22, wherein the first material comprises a crosslinked acrylic polymer, and the second material comprises an acrylic hydrogel-forming polymer.

24. The intraocular lens of claim 22, wherein the second material comprises a polymer selected from the group consisting of poly hydroxyalkyl methacrylates, methyl methacrylate/N-vinyl pyrrolidone-containing copolymers and mixtures thereof.

25. The intraocular lens of claim 12, wherein:
each plate member includes a hinge assembly positioned between the proximal end region and the distal end region; and
the hinge assembly is made of the second material.

26. The intraocular lens of claim 12, wherein the third material is at least as stiff as the first material.

27. The intraocular lens of claim 12, wherein the distal end regions and the optic are formed at least partially from a same cross-linked acrylic polymeric material.

* * * * *

UNITED STATES PATENT AND TRADEMARK OFFICE
CERTIFICATE OF CORRECTION

PATENT NO. : 7,662,180 B2  Page 1 of 1
APPLICATION NO. : 10/314069
DATED : February 16, 2010
INVENTOR(S) : Paul et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1412 days.

Signed and Sealed this

Twenty-eighth Day of December, 2010

David J. Kappos
*Director of the United States Patent and Trademark Office*